United States Patent [19]

Zwingenberger et al.

[11] Patent Number: 5,424,047
[45] Date of Patent: Jun. 13, 1995

[54] STERILIZATION OF MEDICAL INSTRUMENTS, IMPLANTS AND THE LIKE

[75] Inventors: Arthur Zwingenberger, Toronto, Canada; Martin Saupe, Offenbach, Germany

[73] Assignee: Sci-Can, Div. of Lux and Zwingenberger Ltd., Toronto, Canada

[21] Appl. No.: 200,410

[22] Filed: Feb. 23, 1994

[30] Foreign Application Priority Data

Jan. 18, 1994 [EP] European Pat. Off. ......... 94100658.7

[51] Int. Cl.6 ..................... A61L 2/06; A61L 2/24; G05B 9/00
[52] U.S. Cl. ..................... 422/296; 49/477.1; 137/241; 422/26; 422/112; 422/118; 422/297; 422/302
[58] Field of Search ................. 422/26, 28, 118, 292, 422/295, 296, 297, 300, 302, 113, 112; 49/477.1; 137/238, 241

[56] References Cited

U.S. PATENT DOCUMENTS

| | | | |
|---|---|---|---|
| 3,246,947 | 4/1966 | Castle | 422/26 |
| 4,728,504 | 3/1988 | Nichols | 422/297 |
| 5,223,229 | 6/1993 | Brucker | 422/112 X |
| 5,223,231 | 6/1993 | Drake | 422/26 X |
| 5,271,893 | 12/1993 | Newman | 422/26 |

Primary Examiner—Robert J. Warden
Assistant Examiner—L. M. Crawford
Attorney, Agent, or Firm—McAulay, Fisher, Nissen, Goldberg & Kiel

[57] ABSTRACT

A sterilization container for an arrangement for sterilizing medical instruments, implants and the like with steam is disclosed. The arrangement has a steam generator fed by a dispensing pump and has a control device for the sterilizing process. The sterilization container is arranged in such a way that it can be pushed into a holding device in a working connection with the steam generator. The walls of the sterilization container, which is closed on all sides during the sterilizing process so as to be tight against pressure, are formed at least in part by portions of the holding device.

10 Claims, 7 Drawing Sheets

STERILIZATION OF MEDICAL INSTRUMENTS, IMPLANTS AND THE LIKE

BACKGROUND OF THE INVENTION

1. Field of the Invention

The invention is directed to an arrangement for steam sterilization of medical instruments and implants and the like with a steam generator fed by a proportioning or dispensing pump, a sterilization container arranged in such a way that it can be pushed into a holding device in a working connection with the steam generator, and a control device for the sterilizing process as is described and shown in EP 0 429 960 A2.

2. Background Art

In the known arrangement, the sterilization container is constructed as a loose cassette whose base and cover parts are held so as to be pressed together tightly in the holding device during the sterilizing process by flange-like edges with the intermediary of a seal.

However, the construction of the sterilization container as a cassette formed by two parts and closed on all sides against the atmosphere has proven costly to manufacture. Further, close tolerances must be maintained during production, since the associated feed lines and outlet lines must be joined when the cassette is slid into the holding device.

OBJECT AND SUMMARY OF THE INVENTION

Therefore, the primary object of the present invention is to provide a sterilization container whose construction is simple with respect to manufacturing technique and facilitates the loading of instruments and implants and the use of the arrangement.

This object is met according to the invention in that the walls of the sterilization container, which is closed on all sides so as to be tight against pressure during the sterilizing process are, at least in part, portions of the holding device.

According to another feature of the invention, the construction is carried out in such a way that the sterilization container also remains mechanically connected with the associated holding device when loading with the instruments and implants to be sterilized.

It may also be removed in its entirety for maintenance work, e.g. for changing the seals.

The deceptively simple basic idea of the invention, which consists in that walls of the sterilization container which is closed on all sides so as to be tight against pressure during the sterilizing process are allocated at least in part to the holding device receiving the sterilization container during the sterilizing process, is met according to a first embodiment form of the invention in that only the front wall and rear wall are allocated to the sterilization container, while the side wall and the upper and lower walls are allocated to the holding device, wherein at least one perforated plate connecting the front wall and rear wall serves to receive the instruments and implants to be sterilized. At the same time, the sterilization container is held in its working position within the holding device by means of the sealing sleeves which are associated with the front wall and rear wall and seal the space enclosed by the walls against the atmosphere when the sterilization container is pushed in. The steam feed line which opens into the sterilization container space and the air and condensation outlet line which opens into this space are permanently installed in the holding device so that it is no longer necessary to thread or couple these feed and outlet lines into corresponding openings inside the cassette. The guide device which is connected with the holding device so as to be displaceable acts as a supporting means which not only prevents a tilting of the sterilization container when removing it from the holding device, but is constructed at the same time as a collecting trough for moisture dripping from medical instruments and implants coming from the sterilizing space. When the sterilizing process is concluded, the sterilization container is automatically moved out of the holding device into the open position for removal of the sterilized instruments and for reloading without any effort on the part of the user by means of the pressure spring acting on the sterilization container in the holding device. This process is triggered by the locking device which is actuated by pressure or electromagnetically. The locking device likewise has an extremely simple construction, since it need only withstand the spring pressure exerted on the sterilization container. During the sterilizing process, identical pressure ratios prevail on the insides of the front wall and rear wall of the sterilization container so that no resultant forces are exerted on the sterilization container inside the holding device.

Loading is further simplified by the additional construction of the sterilization container, according to a second embodiment form of the invention, as a cup-shaped, rectangular receptacle which is formed by one or more parts and whose longitudinal extension lies transversely to the pushing in direction. A drawer-like arrangement is achieved in that the base surface of the receiving trough is rigidly connected with supporting rails which are supported in the holding device so as to be movable back and forth. The sterilization container can be easily inserted into the holding device thanks to the cover which is held in its inactive position by springs. The cover is arranged so as to be movable vertically inside an exchangeable metal holder in the holding device above the sterilization container and is constructed as a disk supporting in its edge region an elastic rubber seal which contacts the inner wall of the metal holder. Further, the cover has a steam feed in the form of an eccentrically arranged opening which communicates with the interior of the sterilization container in such a way that the cover presses against the upper edges of the sterilization container against the force of springs at the start of the sterilizing process under the pressure of the steam flowing in. During the sterilizing process, the rubber seal tightly seals the sterilizing space against pressure relative to the inner wall of the metal holder and relative to the sterilization container. At the same time, the receptacle trough and accordingly the sterilization container are locked in the recess of the holding device provided for this purpose as a result of the braking forces occurring between the sterilization container and holding device.

To achieve this advantageous effect, the surfaces of the cover facing the sterilization container according to the second embodiment form and the surfaces of the cover facing the recess of the holding device are constructed with different dimensions so that the cover is pressed on the sterilization container, which is open at the top, so as to seal it as a result of the differential pressure occurring while steam is being supplied. When the supply of steam is interrupted, the springs holding the cover pull it into its inactive position within the metal holder, thus releasing the sterilization container so that the latter is freely accessible for removal from the holding device.

The sterilization container, which is divided into subcontainers or partial containers according to another embodiment form of the invention, has special technical advantages with respect to operation, since medical instruments can be placed in each of these partial containers for the sterilizing process depending on their type and dimensions and removed therefrom.

For a better understanding of the present invention, reference is made to the following description and accompanying drawings while the scope of the invention will be pointed out in the appended claims.

BRIEF DESCRIPTION OF THE DRAWINGS

FIG. 5 shows a side view of the holding device with the sterilization container completely pushed in;

DESCRIPTION OF THE PREFERRED EMBODIMENTS

Figure 1:
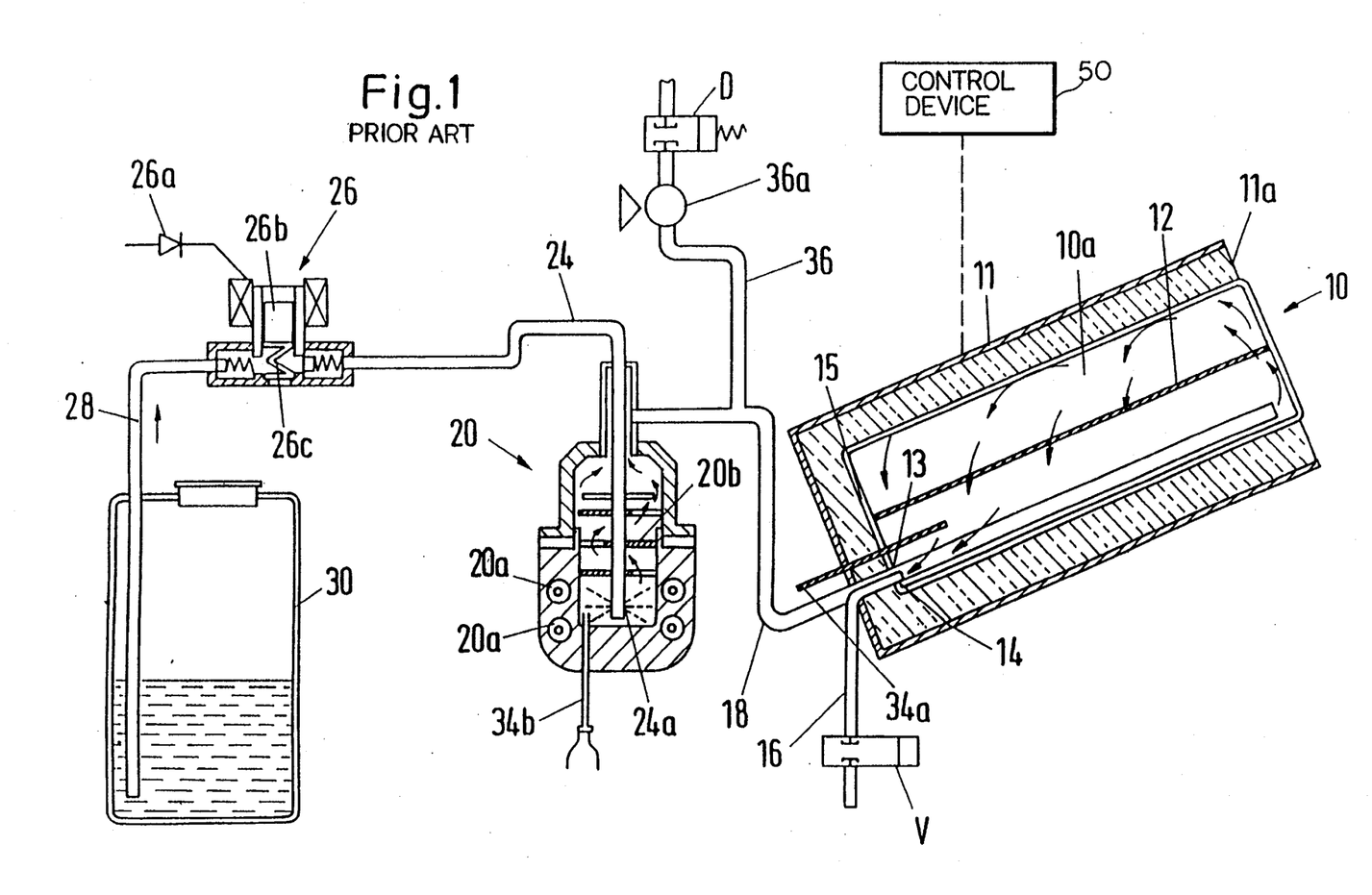
FIG. 1 shows the overview of an arrangement for sterilizing medical instruments and implants with a sterilization container which forms the subject matter of the invention and is arranged in a holding device.

In the arrangement, according to FIG. 1, for sterilizing medical instruments and implants with steam, a sterilization container 10 is used instead of a conventional autoclave. The sterilization container 10 which is constructed as a cassette formed by a base part and cover part and arranged at an angle to the horizontal line can be inserted into a recess of a stationary holding device 11 having thermal insulation 11a. The sterilization container has a receiving plate 12 constructed as a perforated plate for receiving the medical instruments and implants to be sterilized. The holding device 11 has an air and condensation outlet line 16 projecting through an outlet opening 13 in the sterilization container and a steam feed line 18 projecting through an inlet opening 14 into the sterilization container so that these two lines project, at a distance from one another, into the space 10a enclosed by the sterilization container.

The air and condensation outlet line 16 can be connected to the atmosphere via a valve V, while the steam feed line 18 is connected with a steam generator 20. The steam chamber of the steam generator 20 is heated via electrical heating elements 20a and provided with water in a pulsed manner via a feed line 24 having outlet openings 24a at its end. A direct injection of boiling water into the steam feed line 18 is prevented via splash plates 20b arranged in the interior of the steam chamber.

A dispensing pump 26 which communicates, via a suction line 28, with a tank 30 containing distilled water is incorporated in the feed line 24 supplying the steam generator with water. The dispensing pump 26 is driven by means of a piston 26b acting in conjunction with spring 26c and actuated by an electromagnet which is powered via a diode 26a. The temperatures in the steam chamber of the steam generator and in the sterilization container are measured via thermal gauges 34a and 34b.

Finally, the sterilizing chamber can be connected via a branch line 36 and a pressure regulator 36a with a compressed-air source (not shown) which can be switched on via a valve D to cool and dry the instruments and implants at the end of a sterilizing process.

The sequence of a sterilizing process—in which the blast of steam emerging from the steam feed line passes through the sterilization container in a surge—is controlled via a control device shown schematically as 50 in FIG. 1. This process and associated processes for the operation of the described arrangement do not form the subject matter of the invention and are shown and described, for example, in EP 0 429 960 A2.

The first embodiment example of the sterilization container 100 according to the invention is described in the following with reference to FIGS. 2 to 6.

Figure 2:
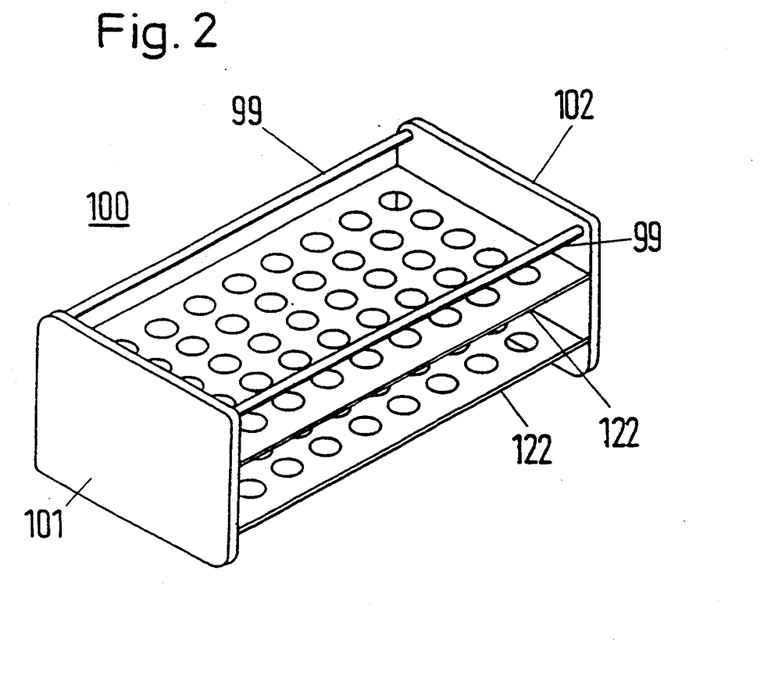
FIG. 2 shows a first embodiment form of a sterilization container for an arrangement according to FIG. 1 in perspective view without seals.

As shown in FIG. 2, the sterilization container 100 has only a front wall 101 and a rear wall 102 which are rigidly connected by connecting members, e.g. by means of pins 99, and by one or more intermediate bases 122 which are constructed as perforated plates to receive the implants and instruments to be sterilized. As will be seen from FIG. 3, the four side walls for this sterilization container are formed by the walls 103, 104, 105 and 106 of the holding device 111 which enclose a square recess in the holding device for receiving the sterilization container which extends longitudinally in the pushing in direction. Accordingly, only the front and rear wall are allocated to the sterilization container, while the side walls, which form a recess which is only open on one side, and the upper wall and lower wall are allocated to the holding device.

Figure 3:
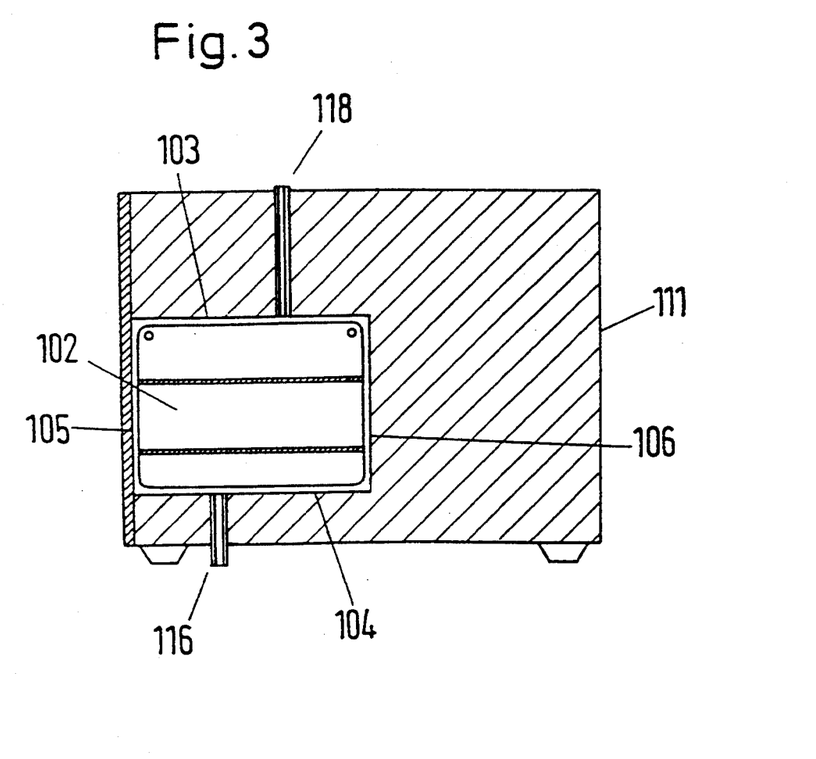
FIG. 3 shows a section through the holding device for receiving the sterilization container according to FIG. 2.

In contrast to the construction according to FIG. 1, the steam feed line 118 in this instance opens out in the upper region in the vicinity of the rear wall 102, i.e. in the wall 103 of the holding device, while the air and condensation outlet 116 open out in the lower region in the vicinity of the front wall 101, i.e. in the wall 104 of the holding device, so that the emerging blast of steam surges through the sterilization container.

Seals 115 of plastic or rubber which are constructed identically and connected with the front wall 101 and rear wall 102 so as to be exchangeable and associated with the front ends, i.e. the front wall and rear wall of the sterilization container 100, serve to seal the sterilizing space which is formed inside the holding device as described in the preceding. Each seal 115 has a lip-shaped edge 120 facing outward and a groove 119 encircling the edge areas of the front and rear wall as shown in particular in FIG. 6.

A cover cap 121 which conceals the recess in the holding device 111 when the sterilization container is pushed in is allocated to the front wall 101 of the sterilization container to ensure a pleasant appearance of the holding device.

This cover cap is part of a guide device 123 associated with the sterilization container 100. The guide device 123 is constructed as a drop vessel and supported so as to be movable back and forth in the holding device by means of rollers 122.

The rear end of the guide device 123 forms a crosspiece 55 which is rigidly connected with the rear wall 102 of the sterilization container 100 via a bar 125.

Figure 4:
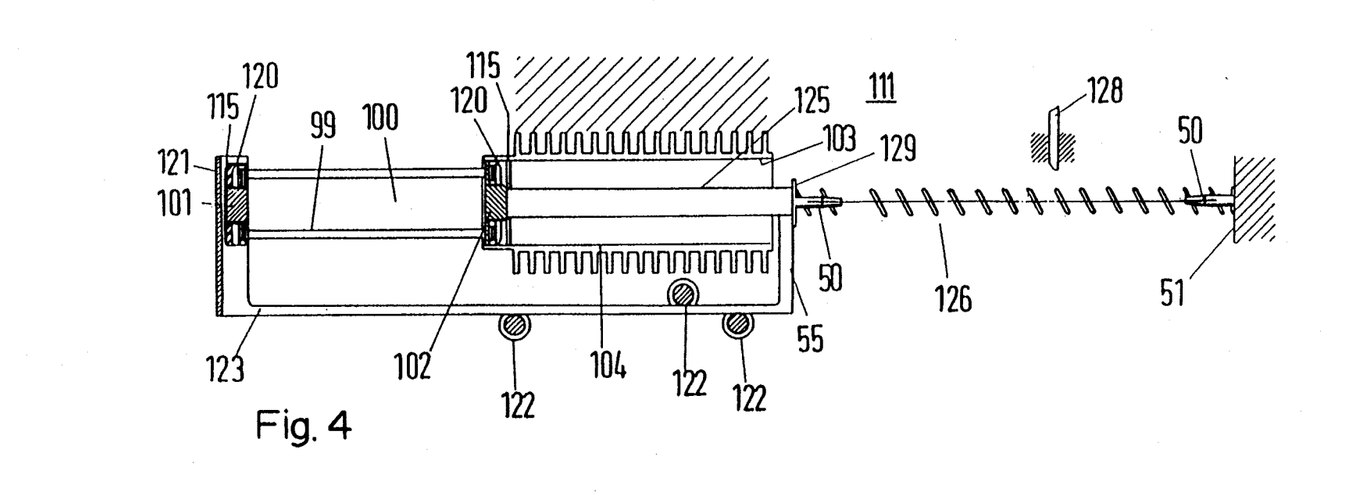
FIG. 4 shows a side view of the holding device with sterilization container removed from the holding device, the longitudinal extension of the sterilization container lying in the inserting direction.
Figure 5:
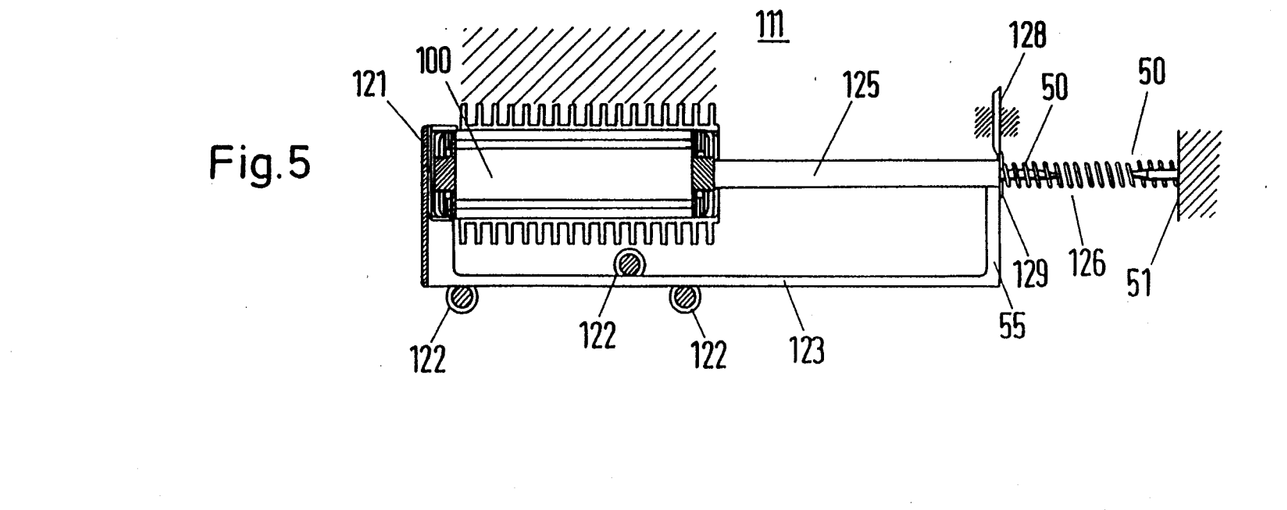
Figure 6:
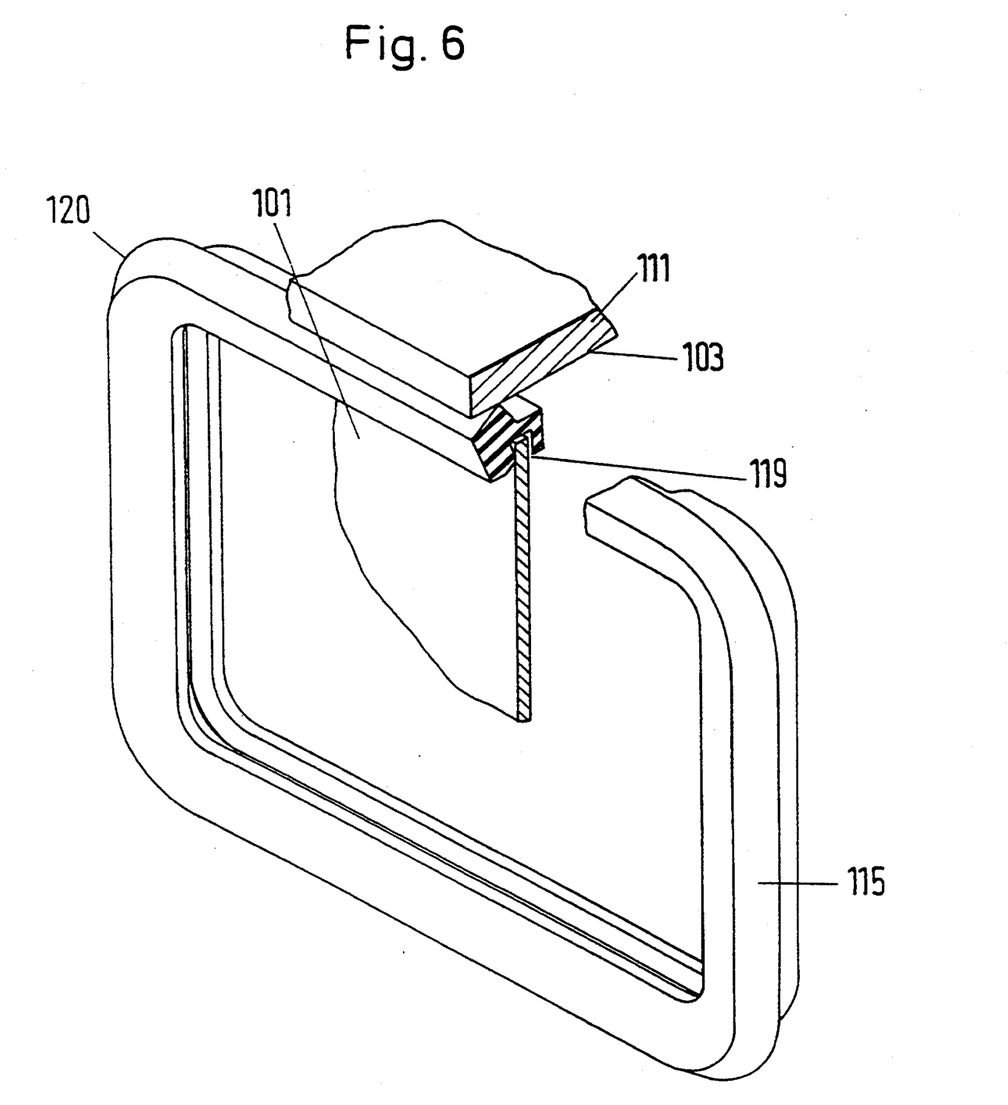
FIG. 6 shows a detail of a sealing element of the sterilization container according to FIGS. 2 to 5 for the front walls.

Finally, as is shown in FIGS. 4 and 5, a spring 126 is provided in the holding device 111. The spring 126 is mounted on projections 50 extending from a rear wall 51 of the holding device 111 and from the bar 125. When relaxed, the spring 126 causes the sterilization container 100 to move into the open position shown in FIG. 4. A lock in the form of a stop 128 is provided in order to hold the inserted sterilization container in the pushed in position in which the spring 126 is tensioned. This stop 128 can be actuated electromagnetically or via a pressure means actuating member in a manner not shown here, the stop 128 engaging behind a corresponding stop 129 of the holding device as soon as the latter is moved into the completely pushed in position shown in FIG. 5.

When the sterilization container is pushed in, the lip-shaped edges 120 of the seal 115 which project over the circumferential area—front and rear wall—of the sterilization container tightly contact the walls 103/104 and 105/106 of the holding device during a sterilizing process under the influence of the steam pressure and in so doing tightly hold the sterilization container in its pushed in position in the holding device (compare FIG. 5).

Finally, the sterilization container can be acted upon by a damping device, known per se, which converts the sudden ejecting movement of the sterilization container caused by the spring 126 into a continuously flowing exiting movement.

Figure 7:
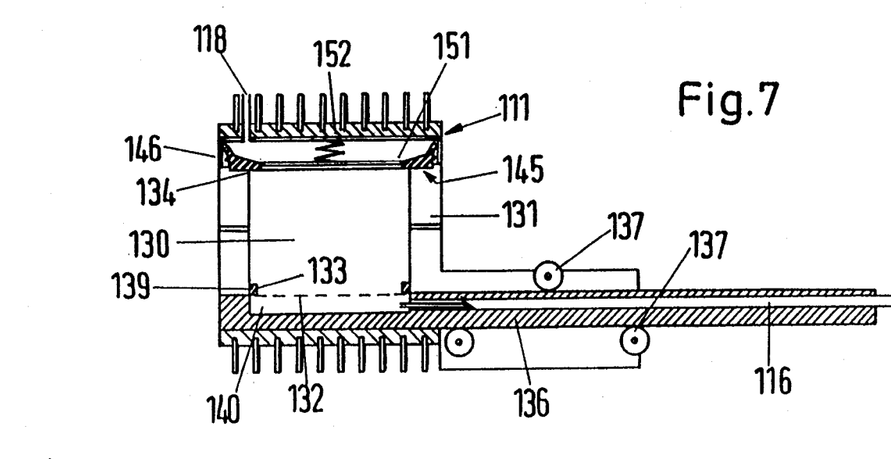
FIG. 7 shows a section through a second embodiment form of a sterilization container in the working position inside the holding device of an arrangement according to FIG. 1 with its longitudinal extension lying transversely to the insertion direction.
Figure 7A:
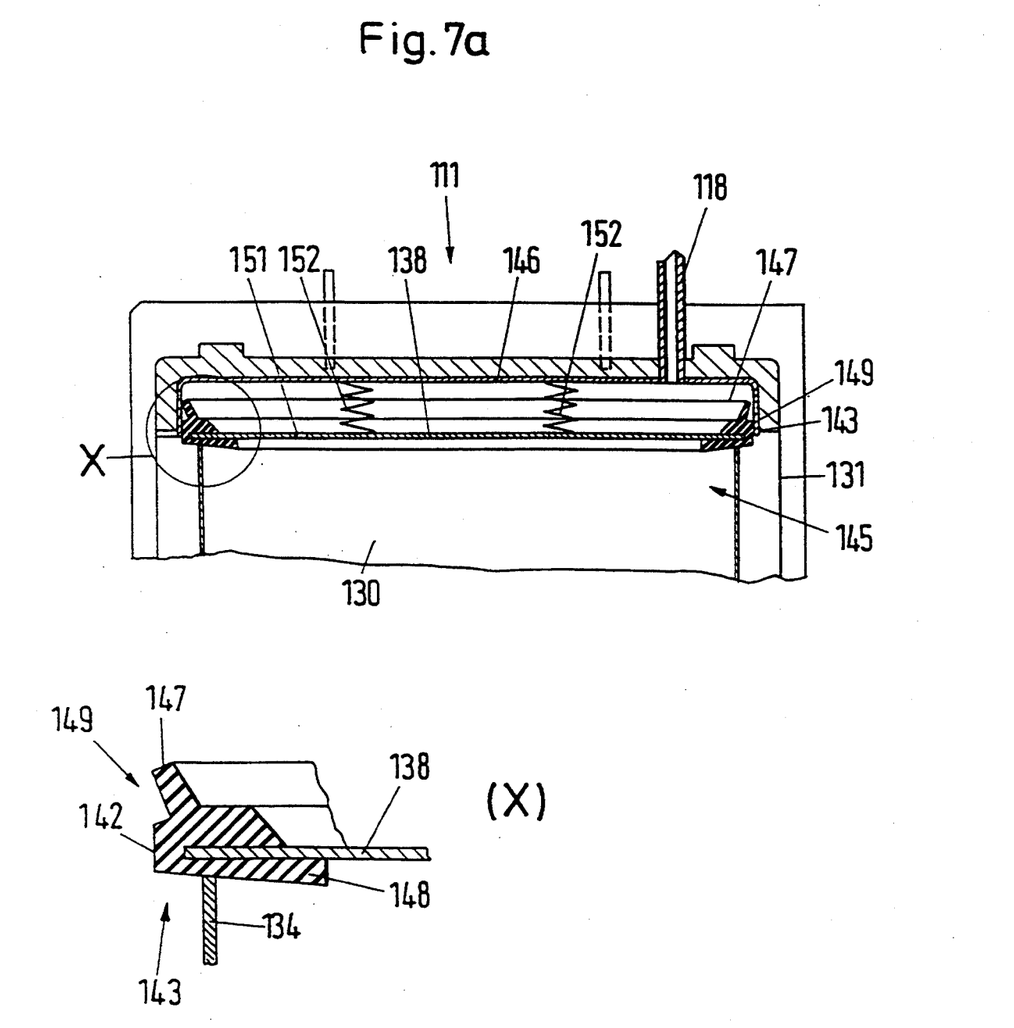
FIG. 7a is an enlarged view of the cover of the sterilization container according to FIG. 7.
Figure 8:
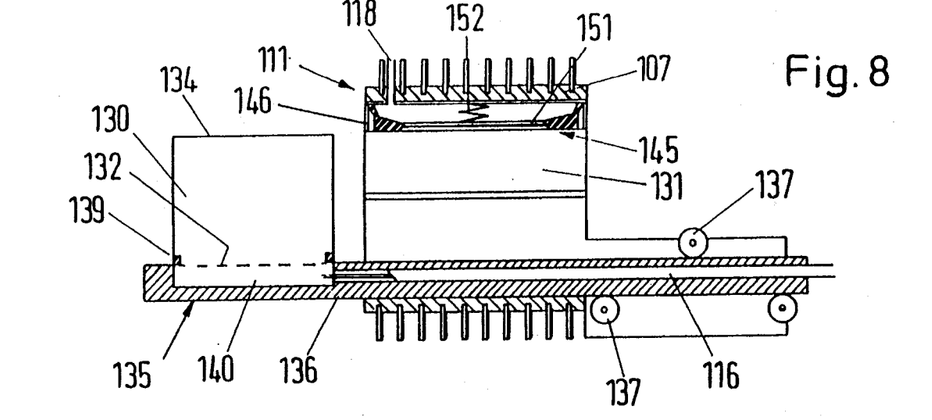
FIG. 8 shows a section through the sterilization container according to FIG. 7 in the position enabling charging with instruments and implants to be sterilized.

According to another embodiment form of the sterilization container which is designated in its entirety by 130 according to FIGS. 7, 7a, and 8, this sterilization container 130 is constructed as a square cup, i.e. with front wall and rear wall and with side walls and a perforated base surface 132. The sterilization container 130 has, adjacent to its perforated base surface 132, a drawn in edge 133 which is open at the top. A rectangular, shell-like receptacle 135 which is closed at the bottom and adapted to the circumference of the sterilization container is allocated to the base surface 132 for accommodating the sterilization container 130 in a detachable manner. This shell-shaped receptacle can be transferred from a receiving position (FIG. 8) outside the holding device into a working position (FIG. 7) inside the holding device within a recess 131 provided for this purpose and vice versa by means of a rail guide 136 whose supporting rails are guided between rollers 137 supported in the holding device 111. A surrounding seal 139 is arranged between the receptacle 135 and the drawn in edge 133. The seal 139 seals the perforated base surface 132 of the sterilization container against the atmosphere in the inserted position in the receptacle 135.

The sterilization container, according to this embodiment form, whose longitudinal extension lies transversely to the pushing in direction is arranged in the recess 131 of the holding device 111 provided for this purpose in the manner of a drawer which can be completely pulled out. The upper wall 107 of the holding device 111 with reference to FIGS. 7 and 8 forms the wall (not shown in the drawing) of the sterilization container 130 in a manner which will be described in more detail.

The air and condensation outlet 116 in the form of a pipe which communicates with the space 140 below the base surface 132 of the receptacle 135 opens out in the shell-shaped portion of the receptacle 135.

As is shown in particular in FIG. 7a, the sterilization container is covered by a rectangular lid or cover 145 which is suspended in the manner of a piston in a frame-like metal holder 146 inside the recess 131 in the holding device 111, which recess 131 receives the sterilization container 130. The lid or cover 145 is suspended so as to be stationary, but in such a way that it can be moved up and down via springs 152 at the metal holder 146. The lid 145 projects over the upper open region, i.e. the upper edges 134 of the sterilization container 130, on all sides and supports a sealing profile 143 which is roughly L-shaped in cross section. The lower leg 148 elongated to accommodate a disk 138 forming the lid and to cover the upper edges 134 of the sterilization container as is shown in particular in detail X, whereas the outer leg 149 with reference to FIG. 7a contacts the inner wall of the metal holder 146 while forming a guide surface 142. A lip 147 of the leg 149 forms an additional sealing surface of the lid 145. The lower surface of the leg 148 of the sealing profile, which is roughly L-shaped in cross section, tightly contacts the edges 134 of the sterilization container 130 in the operating state. The lid has an eccentric opening 151 which penetrates it and connects the space enclosed by the sterilization container with the open space above the lid inside the metal holder 146.

The steam feed line 118 opens above the lid into the recess 131 of the holding device 111 receiving the sterilization container 130. Since the covered surface of the sterilization container is smaller than the free surface of the lid facing the steam feed line 118, the lid is moved by the steam pressure against the upper edges 134 of the sterilization container against the action of the springs 152 due to the resulting differential pressure and closes the interior of the sterilization container so as to be tight against pressure. This pressure difference between the upper and lower surface of the lid at the same time holds the sterilization container in the pushed in position in the recess due to the braking forces occurring in this sealing process between the sterilization container and the holding device and housing.

When the steam pressure falls off, the springs 152 draw the lid into its rest position inside the metal holder 146 and the sterilization container 130 is released.

The pressure spring 126 causing the ejection of the sterilization container, which was already described in connection with FIGS. 4 and 5, is also provided in this embodiment form.

Figure 9:
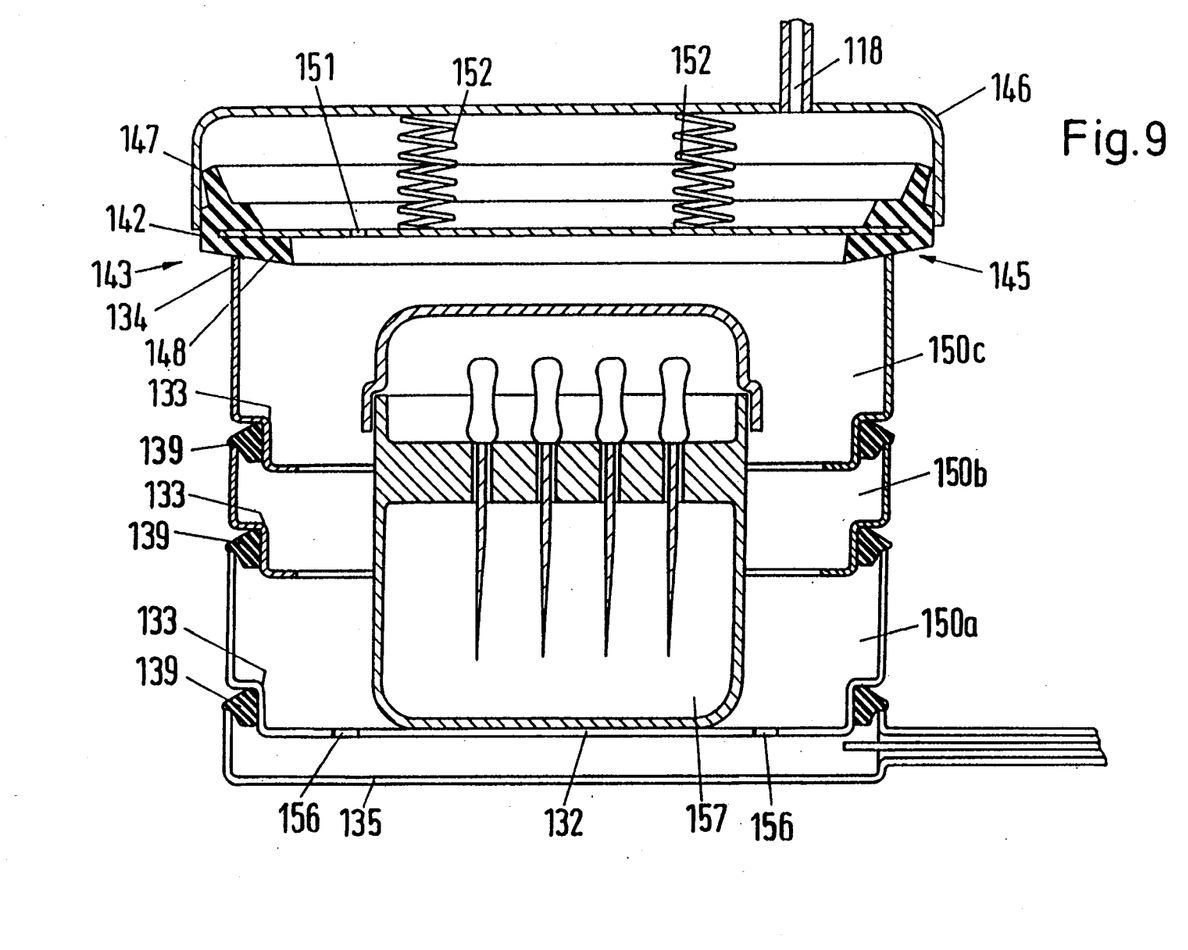
FIG. 9 shows a further development of the embodiment form of the sterilization container according to FIG. 7 in section.

Another construction of the sterilization container is shown in FIG. 9. This construction uses the same holding device as that described with reference to the embodiment example according to FIGS. 7 to 8.

In this instance, a plurality of partial containers 150a, 150b and 150c (standard tray) are provided instead of an integral sterilization container. The available vertical area of the recess 131 of the holding device 111 corresponding to FIG. 9 (but specifically shown in FIGS. 7 and 8) is divided into three partial regions 150a, 150b and 150c. The partial containers are constructed in such a way that they can be stacked. For this purpose, each of the partial containers 150 likewise has a drawn in edge region 133 which corresponds to the upper edge region of the associated partial container, a seal 139 being arranged in each edge region 133. The lowest seal of each stack of partial containers is associated with the receptacle 135 as was described and shown in the embodiment example according to FIGS. 7 to 8. The open surface region of the uppermost partial container is also closed in a pressure-tight manner during a sterilizing process by means of the rectangular lid or covering 145 which was described in detail with reference to FIGS. 7 to 8 so that the entire arrangement of partial containers is sealed against the atmosphere during the sterilizing processes and held in the recess of the holding device. The base surfaces of the individual partial containers have perforations for letting through steam. The steam is also supplied in this instance via the opening 151 in the lid and the air and condensation are guided out via the pipe 116 in the region of the rail guide 136.

As is further shown in FIG. 9, openings 156 which are flush with one another and, for example, rectangular, are provided in the base surfaces 132 of the partial container 150 which form a receiving space extending over a plurality of partial containers for instruments and/or implants arranged in a stand 157.

Further, a partial container which is constructed as a lid with perforated base surface 132 can be associated with the partial containers.

While the foregoing description and drawings represent the preferred embodiments of the present invention, it will be obvious to those skilled in the art that various changes and modifications may be made therein without departing from the true spirit and scope of the present invention.

More particularly, sterilization containers which are at least partially open and can be closed in a pressure-tight manner automatically when moving them into the working position inside the associated recesses in the holding device and connected with the steam feedline and air outlet can be used instead of a sterilization container which is closed on all sides.

What is claimed is:

1. In an arrangement for sterilizing medical instruments and implants with steam having a steam generator supplied by a dispensing pump, a sterilization container being defined by a plurality of walls so that it can be pushed into a holding means in working relationship with the steam generator, and control means for the sterilizing process, the improvement comprising:
the walls of the sterilization container being formed at least in part by portions of the holding means;
the holding means including a cover for the sterilization container, said cover automatically closing said sterilization container in a pressure-tight manner when the sterilization process is initiated; and
wherein a closed sterilization space is defined by the combination of the sterilization container and the holding means when the sterilization container is inserted in said holding means.

2. The arrangement according to claim 1, wherein a seal is arranged relative to a lower side and to an upper side of the sterilization container, which seals a recess enclosed by the holding means against the atmosphere when the sterilization container is pushed into the holding means.

3. The arrangement according to claim 2, wherein said cover is held in its inactive position by springs and has a disk serving as support for an elastic rubber seal forming its edge region and is arranged so as to be movable vertically inside an exchangeable metal holder in the holding means above the sterilization container, wherein surfaces of the cover which face the sterilization container and the surfaces of the cover which face the recess of the holding means are constructed with different dimensions, and wherein the cover has a steam feed in the form of an eccentrically arranged opening which communicates with an interior of the sterilization container.

4. The arrangement according to claim 3, wherein the rubber seal is roughly L-shaped in cross section and has legs, a portion of those legs of the rubber seal which form a base enclose a disk of the cover and form a sealing surface, while the remaining legs have a guide surface and a sealing lip contacting a lateral inner surface of the metal holder.

5. The arrangement according to claim 4, wherein the sterilization container is divided into partial containers of identical surface area which carry seals, the vertical dimensions of the partial containers being selected in such a way that all partial containers can be closed so as to be pressure-tight by the same cover within the recess of the holding means.

6. The arrangement according to claim 1, wherein the holding means includes a receiving means for receiving the sterilization container in a detachable manner, said receiving means being displaceably supported by the holding means.

7. The arrangement according to claim 1, wherein a steam feed line, which is permanently installed in the holding means, and an air and condensation outlet line open into said sterilization space.

8. The arrangement according to claim 1, wherein the holding means includes a supporting means for collecting moisture dripping from medical instruments and implants and exiting said sterilization space, said supporting means being displaceably connected to the holding means.

9. The arrangement according to claim 1, wherein a pressure spring is provided for causing the ejection of the sterilization container and wherein a locking means for triggering the ejecting process of the sterilization container is provided in association with the pressure spring, the locking means being actuated by pressure or electromagnetic force.

10. The arrangement according to claim 1, wherein the sterilization container is constructed as a cup-shaped, rectangular receptacle having a longitudinal extension located transverse to the direction of pushing the sterilization container into the holding means, and wherein the holding means includes a receiving means for receiving the sterilization container in a detachable manner, the receiving means being guided by rails, and wherein an air and condensation outlet line is arranged in the receiving means.

* * * * *